(12) United States Patent
Mojmeli Renani et al.

(10) Patent No.: US 8,784,773 B2
(45) Date of Patent: Jul. 22, 2014

(54) HYDROGEL NANOCOMPOSITE WOUND DRESSING AND A METHOD OF SYNTHESIZING THE SAME

(76) Inventors: Mohammad Mojmeli Renani, Tehran (IR); Mehran Solati Hashjin, Tehran (IR); Mohammad Rabiee, Tehran (IR); Yasaman Ganji, Tehran (IR); Leila Parsa, Esfahan (IR); Masoomeh Mojmeli Renani, Esfahan (IR)

( * ) Notice: Subject to any disclaimer, the term of this patent is extended or adjusted under 35 U.S.C. 154(b) by 133 days.

(21) Appl. No.: 13/405,243

(22) Filed: Feb. 25, 2012

(65) Prior Publication Data

US 2013/0224256 A1     Aug. 29, 2013

(51) Int. Cl.
| | |
|---|---|
| *A61M 36/14* | (2006.01) |
| *A61K 38/08* | (2006.01) |
| *A61K 51/08* | (2006.01) |
| *A61M 31/00* | (2006.01) |
| *A61F 5/44* | (2006.01) |
| *A61F 13/00* | (2006.01) |

(52) U.S. Cl.
CPC .............. *A61K 38/08* (2013.01); *A61K 51/088* (2013.01); *A61M 31/002* (2013.01); *A61F 5/44* (2013.01); *A61F 13/00* (2013.01); *Y10S 977/775* (2013.01)
USPC .................. 424/1.69; 424/78.27; 977/775

(58) Field of Classification Search
CPC ... A61K 38/08; A61K 51/088; A61M 31/002; A61F 5/44; A61F 13/00
USPC ................................. 424/1.69, 78.27; 977/775
See application file for complete search history.

(56) References Cited

U.S. PATENT DOCUMENTS

| | | | | |
|---|---|---|---|---|
| 2005/0115462 | A1* | 6/2005 | Disalvo et al. ................ | 106/403 |
| 2006/0034905 | A1* | 2/2006 | Singh et al. .................... | 424/449 |

OTHER PUBLICATIONS

Mehrdad Kokabi, et al, PVA-Clay Nanocomposite Hydrogels for Wound Dressing, 43 Eur. Pol. J 773 (2007).*
Masao Tanihara, et al, Thrombin-Sensitive Peptide Linkers for Biological Signal Responsive Drug Release Systems, 19 Peptides 421 (1998).*

* cited by examiner

*Primary Examiner* — Sean Basquill
(74) *Attorney, Agent, or Firm* — Barry Choobin; Patent 360 LLC

(57) ABSTRACT

The various embodiments herein provide hydrogel nanocomposite wound dressing comprising a polymeric basal matrix, a reinforcing agent, a biological sensor and an antibiotic for a slow release in a wound when applied. The polymeric basal matrix is made up of polyvinyl alcohol polymer with an amount of 1-15% by weight. The reinforcing agent comprises clay nanoparticles to inhibit a sudden drug release. The clay nanoparticles comprise montmorillonite nano particles with an amount of 0-2% by weight. The biological sensor is a peptide chain. The peptide chain is thrombin sensitive with an amount from 50 to 200 mg. The antibiotic is gentamycine with an amount of 1-3% by weight. The embodiments herein also provide a method of synthesizing the hydrogel nanocomposite wound dressing.

15 Claims, 17 Drawing Sheets

HYDROGEL NANOCOMPOSITE WOUND DRESSING AND A METHOD OF SYNTHESIZING THE SAME

BACKGROUND

1. Technical Field

The embodiments herein generally relate to a wound dressing and particularly to a nano-composite wound dressing. The embodiments herein more particularly relate to a controlled drug release wound dressing that is sensitive to infection. The embodiments herein also relate to a method of synthesizing the nano-composite wound dressing.

2. Description of the Related Art

Many microorganisms like bacteria, viruses or fungi can cause infection in wounds. Most of the infectious wounds begin with bacteria invasion like *staphylococcus* and *Pseudomonas* bacteria. Polluted water, dust or other materials help the bacteria to create infection. The most important method of preventing infection is using antibiotics.

The smart hydrogel with response to infection has been introduced by Masao Tanihara et al. in 1997, which composed of a 3D structure of polyvinyl alcohol (PVA) linked to a peptide group. But a disadvantage of this kind of smart hydrogels wound dressings is the sudden release of drug. This leads to a complete release of a drug in a short period of time instead of their slow release requirement for a treatment of the infection.

Wound dressings cover the wounds and improve the wound repair conditions. Mechanical properties of these covers, for example, tensile strength, elongation, adherence and stiffness are the most important factors in the study of functional wound dressings. An ideal wound dressing should full-fill all the desired mechanical properties, optimum humidity on the wound surface and speeding up the repair process/mechanism.

The gels or nanocomposite hydrogels are similar to other polymer-clay nanocomposites in a distribution of layer clay silicates in their structures. The clay layers can distribute in a gel matrix among three ways: 2-phases micro-composites, diffusion nanocomposites, and diffusion nanocomposites with layer clay silicates. There are some major differences in the order of polymeric chains structure of nanocomposite gels in comparison with other nanocomposite materials. There are some cross linking of polymeric chains in the clay layers and also inside the chains in the nanocomposite gels. These linking provide a complex 3D structure with the association of clay layers. In most cases, an order of silicate layers is disrupted by cross linking the nanocomposite gels. Therefore, these nanocomposite materials usually have a penetrative structure with a change of silicate clay layers structure.

In a preparation of nanocomposite gels, the most convenient way is a penetration of polymeric chains into the clay layers and then cross linking these chains. Some other polymeric-clay nanocomposite preparation methods reported elsewhere are in situ polymerization. Networking and cross linking methods in nanocomposite gels are same as used in other polymeric gels like use of networking agents, $\gamma$ rays, heating and cooling treatment, etc. Nanocomposite gels have the potential of high swelling in liquid environment like other polymeric gels.

3D structures are composed of linked polymeric chains with many applications in different fields. Water or liquid materials are the major chemical components of these polymeric products (more than 70% wt). Therefore, they have low mechanical strength. These low mechanical properties of polymeric gels are problematic in biomedical uses, which are more problematic in hydrogel wound dressings.

Low tensile strength and high adherence causes wound dressing to adhere into wound tightly in some cases. This event disrupts wound repair and also makes it difficult to change the wound dressing without physiological saline solutions. Combination of polymeric hydrogels and nanocomposites is an effective way to solve these problems.

Hence there is a need for developing a wound dressing material loaded with a drug that is capable of slowly releasing a drug and preventing from infection in wounds.

The above mentioned shortcomings, disadvantages and problems are addressed herein and which will be understood by reading and studying the following specification.

OBJECTIVES OF THE EMBODIMENTS

The primary object of the embodiments herein is to provide a smart hydrogel nano-composite wound dressing with an antibiotic.

Another object of the embodiments herein is to provide a hydrogel nano-composite wound dressing to enable a controllable drug release system.

Yet another object of the embodiments herein is to provide a hydrogel nano-composite wound dressing that releases antibiotic during a microbial infection.

Yet another object of the embodiments herein is to provide a hydrogel nano-composite wound dressing to inhibit injuries made by a long-term use of the antibiotics.

Yet another object of the embodiments herein is to provide a hydrogel nano-composite wound dressing that is mechanically strong.

Yet another object of the embodiments herein is to provide a hydrogel nano-composite wound dressing that does not require a repetitive application or replacement.

Yet another object of the embodiments herein is to provide a hydrogel nano-composite wound dressing with an ability to release antibiotic during microbial infection and to prevent the long term side effects of using antibiotics in liver and kidney when taken for in diseases.

Yet another object of the embodiments herein is to provide an easy and novel method of synthesizing a hydrogel nano-composite wound dressing.

These and other objects and advantages of the embodiments herein will become readily apparent from the following detailed description taken in conjunction with the accompanying drawings.

SUMMARY

The various embodiments herein provide a hydrogel nano-composite wound dressing. The wound dressing comprises a polymeric basal matrix, a reinforcing agent, a biological sensor and an antibiotic. The polymeric basal matrix is made up of polyvinyl alcohol polymer with an amount of 1-15% by weight. The reinforcing agent comprises clay nanoparticles to inhibit sudden drug release. The clay nanoparticles comprise montmorillonite nano particles with an amount of 0-2% by weight. The biological sensor is a peptide chain. The peptide chain is thrombin sensitive with an amount from 50 to 200 mg. The antibiotic is gentamycin with an amount of 1-3% by weight. The antibiotic is slowly released in a wound. The polyvinyl alcohol polymer has a degree of polymerization of 1700. The polyvinyl alcohol polymer has a molecular weight of 26300-30000. The montmorillonite nano particles have a saponification value of greater than 98%. The montmorillonite nanoparticles are both modified and non-modified montmorillonite nanoparticles. The modified and non modified montmorillonite nanoparticles have a particle size of about 2 nm. The peptide chain is Gly-(D)Phe-Pro-Arg-Gly-Phe-Ala-Gly-Gly.

According to one embodiment herein, the hydrogel nanocomposite wound dressing is transparent. The antibiotic is released in 20 hours and reaches to a maximum level in first 2 hours. The antibiotic is released after a breaking down of the peptide chain. The hydrogel nanocomposite wound dressing is infection absorbent and prevents from infection in non-infectious wounds by preventing a microbial permeation. The hydrogel nanocomposite wound dressing is non-toxic and treats infectious wound without a need of repetitive replacement.

According to an embodiment herein, a method of synthesizing a hydrogel nanocomposite wound dressing comprises carboxylating a Polyvinyl alcohol nanocomposite hydrogel structure, linking a peptide chain with the carboxylated PVA nanocomposite hydrogel structure and linking an antibiotic with a peptide chain. The antibiotic herein is gentamycin.

The step of carboxylating a PVA nanocomposite hydrogel structure further includes preparing aqueous solutions of Polyvinyl alcohol (PVA) with a percentage of 1-15% and clay with a percentage of 1-10%. A thermal treatment process is provided to the prepared aqueous solutions of the PVA and the clay. The thermal treatment process involves heating and cooling of the solutions. The heating process involves heating the solution at +20° C. for 24 hours and the cooling process involves cooling at −20° C. for 24 hours. The process of thermal treatment is performed twice in a cycle. Carboxylating the thermally treated solution by adding dimethyl sulfoxide. Succinic anhydride and pyridine are added to the solution added with dimethyl sulfoxide. The thermally treated solution with dimethyl sulfoxide, succinic anhydride and pyridine is held at 10° C. for an overnight to complete the carboxylation reaction to extract a resultant hydrogel. the extracted resultant hydrogel is washed with Phosphate Buffer Saline (PBS) to obtain a first resultant solution. The first resultant solution is washed with Distilled Deionized Water (DDW) for several times to obtain a second resultant solution. The second resultant solution is washed with dimethyl formamide for several times to remove the unreacted materials.

The step of linking a peptide chain with the carboxylated PVA nanocomposite hydrogel structure further includes holding the washed carboxylated PVA nanocomposite hydrogel with a solution of formamide having a volume of 10 cc to obtain a sample. The solution of formamide contains 50 mg of N-Hydroxysuccinimide (HOSU) and 80 mg of 1-Ethyl-3-(3-dimethylaminopropyl)carbodiimide (EDC). The sample is placed in a solution of peptide chain with an amount of 120 mg for an overnight and the sample placed in a solution of peptide chain is washed with PBS for several times to remove all remaining unreacted materials.

The step of linking the gentamycine with the peptide chain further includes mechanically stirring a solution of linked peptide with carboxylated PVA nanocomposite hydrogel for 24 hours in a solution comprising gentamycin with an amount of 7 g and EDC with an amount of 25 mg.

According to one embodiment herein, a nanocomposite wound dressing comprises one polymeric basal phase, nanoparticles as strengthening phase and inhibitor of sudden drug release, peptide chain as a biologic sensor which is sensitive to thrombin in infectious wound and antibiotics. The peptide chain makes the composite smart. The polymeric phase is made up of polyvinyl alcohol (PVA) with degree of polymerization of 1700. The polymeric phase has a molecular weight between 26300 and 30000 and presents in an amount of about 1-15% by weight. Clay nanoparticles are made up of montmorillonite (MONT) nanoparticles with a saponification value of greater than 98% and weight percentage of 0-2. Montmorillonite is both modified and non-modified nanoparticles. Peptide chain is Gly-(D)Phe-Pro-Arg-Gly-Phe-Ala-Gly-Gly presented in an amount from 50 to 200 mg. Antibiotic is gentamycine with 1-3% by weight. Nanocomposite hydrogel is completely transparent. Nanocomposite hydrogel is infection absorbent. Nanocomposite hydrogel prevents from infection in non-infectious wounds. Nanocomposite hydrogel release drug by fracture in peptide chains according to extent of infection in 20 hours. Release of drug is directly due to montmorillonite nanoparticles. Nanocomposite hydrogel prevents from microbial permeation. Nanocomposite hydrogel is nontoxic. Nanoclay improves the mechanical properties. Nanoclay controls the drug release. Modified montmorillonite has the potential of infectious wound treatment without need to repetitious replacement.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
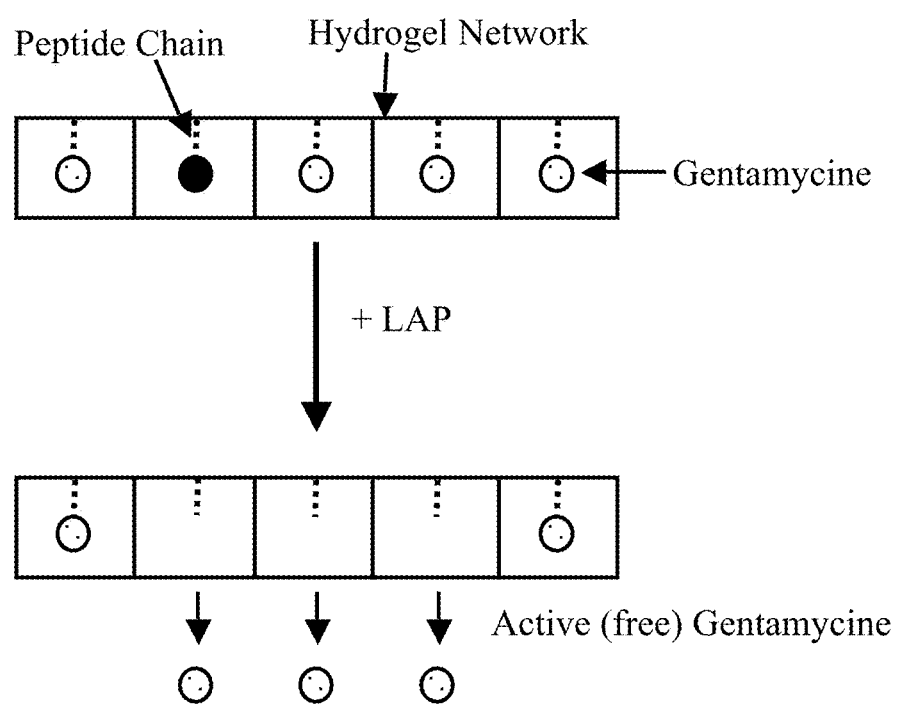
FIG. 1 shows the response of smart hydrogel to infection and increase of thrombin activity, according to the embodiments herein.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

In the embodiments herein, modification and optimization of smart hydrogel properties and fabrication of nanocomposite wound dressing with sensitivity to infection is provided. The embodiments herein provide a controllable drug release system. The controllable drug release system is a smart nanocomposite hydrogel. According to the embodiments herein, the smart nanocomposite hydrogel is based on Polyvinyl alcohol (PVA) as a polymeric matrix, modified and non-modified Montmorillonite (i.e. OMONT and MONT, respectively) as a reinforcing agent, gentamycine as antibiotic and peptide chain as thrombin sensitive biological sensor.

The system consists of a drug vector that releases antibiotics during a microbial infection. The controllable drug release inhibits the injuries made by long-term use of antibiotics. In this kind of system, the properties of hydrogel wound dressing are improved and modified that leads to introducing a smart hydrogel sensitive to infections. In addition, using a drug vector omits or decreases taking injections or oral intake of antibiotics in infectious wounds.

Smart wound dressing is composed of PVA and peptide groups. Peptide chain acts as a biological sensor against thrombin. It also links gentamycine—as antimicrobial drug—into hydrogel structure. Peptide sensor is selected based on amino acid bases. In a normal condition, thrombin can be found as a passive pre-thrombin enzyme in human blood with a concentration about 150 mg/l. The thrombin activity increases in microbial infectious wounds by conversion of prothrombin into thrombin. The increase in thrombin activity is considered as a stimulator of smart hydrogel with response to infection. By placing the hydrogel on wound site, thrombin activity increases and leads to fracture of thrombin sensitive peptide chains. Consequently, peptide-linked-inactive gentamycine is released and acts upon the infection.

The inactive gentamycine becomes active in presence of Leucin Aminopeptidase (LAP) found in infectious wounds. LAP can easily separate gentamycine from peptide and pure gentamycine is produced. Loaded drug is completely released in 4 hours.

According to an embodiment herein, the preparation of the smart nanocomposite hydrogel material comprises three separate steps. The steps are: first, carboxylation of PVA nanocomposite hydrogel, second, linking between peptide chain and hydrogel structure and third, linking between gentamycine and the peptide chain. PVA has a degree of polymerization of 1700 and a saponification value of about 98%. Modified and non modified MONT nanoparticles have a particle size of about 2 nm. The peptide chain is Gly-(D)Phe-Pro-Arg-Gly-Phe-Ala-Gly-Gly and the antibiotic is gentamycine.

Use of nanoclay particles improves hydrogel wound dressing properties. Montmorillonite or MONT clays contain the best structure and properties for composing with polymeric nano composites. For an instance, MONT nanoparticles provide stronger bond with polymeric chain of matrix in comparison with other clays caused a more homogenous structure and better properties in nanocomposite. Since the hydrogel dressing have low strength and mechanical properties, small amount of biocompatible and non toxic MONT nanoparticles is used as reinforcing agent. In addition, these nanoparticles increase releasing time up to 20 hours which is one of the most important benefits in nanocomposite wound dressings.

Experimental Data

The smart nanocomposite hydrogel was based on PVA as a polymeric matrix, modified and non modified montmorillonite as a reinforcing agent, gentamycine as antibiotic and peptide chain as thrombin sensitive biological sensor. Preparation of this material was laid down in three separate steps: carboxylation of PVA nanocomposite hydrogel, linking between peptide chain and hydrogel structure, and linking between gentamycine and peptide chain.

The preparation procedure briefly contains the following steps: an aqueous solution with 15% PVA by weight and different weight percentage of clay in the range of 1-10% was prepared. The prepared solution was thermally (heating and cooling) treated twice for cross linking by heating at +20° C. for 24 hours and cooling at −20° C. for 24 hours. The above solution was carboxylated by dimethyl sulfoxide and succinic anhydride and pyridine and held at 10° C. for an overnight to complete the reaction. A resultant hydrogel (PVA-COOH) was extracted from the above solution and finally washed with PBS several times to remove any unreacted materials.

The obtained solution was washed with DDW several times to remove the unreacted materials. All the samples were washed with dimethyl formamide several times. Then, the samples were held in a solution of 10 cc formamide containing 50 mg HOSU and 80 mg EDC. The samples were placed in a solution of 120 mg peptide for an overnight. 5 g of each samples were washed with PBS several times to remove all remaining unreacted materials. The samples were mechanically stirred in a solution of 7 g of gentamycine and 25 mg of EDC for 24 hours for linking between the gentamycine and the peptide chain.

Aqueous solution was prepared by adding several predetermined percentage of MONT into distilled deionized water (DDW). Then, the solution was heated up to 90° C. and PVA was gradually added during a mechanical stirring. The mechanical stirring was done by centrifugation. Some DDW was added during the process to recover the water evaporated caused by heating up of the solution. Solution viscosity was low in the beginning of mixing and centrifugation speed of about 200 rpm was sufficient. But viscosity increases during the process so the speed should be reduced to prevent formation of air bubbles. The prepared solution was kept in plastic molds with caps.

Table 1 includes weight percentages of all the components in different samples.

| Sample ID | OMONT (modified) | MONT (non-modified) | PVA | Gentamycine |
|---|---|---|---|---|
| 1 | — | — | 15 | — |
| 2 | — | 0.75 | 15 | — |
| 3 | — | 1.5 | 15 | — |
| 4 | 0.3 | — | 15 | — |
| 5 | 0.75 | — | 15 | — |
| 6 | 1.05 | — | 15 | — |
| 7 | 1.5 | — | 15 | — |
| 8 | — | — | 15 | 1.5 |
| 9 | — | 0.75 | 15 | 1.5 |
| 10 | — | 1.5 | 15 | 1.5 |
| 11 | 0.3 | — | 15 | 1.5 |
| 12 | 0.75 | — | 15 | 1.5 |
| 13 | 1.05 | — | 15 | 1.5 |
| 14 | 1.5 | — | 15 | 1.5 |

For thermal treatment of nanocomposite two stage of heating and cooling are carried out. The sample is held in +20° C. for 24 hours in heating stage and −20° C. for 24 hours in cooling stage. This kind of treatment leads to a cross linking of polymer chains. For carboxylation of samples No. 8 to 14 prepared hydrogel was added to Dimethylsolfoxide containing succinic anhydride and pyridine. Solution was hold at 10° C. for an overnight to complete the reaction. After that, the resultant hydrogel (PVA-COOH) was extracted from the solution and washed with PBS several times to remove unreacted materials.

Gentamycine is a sugar derived antibiotics with antibacterial properties particularly against staphylococcus and pseudomonas bacteria. A solution of powder form of peptide was prepared and used.

FIG. 1 shows the response of smart hydrogel to infection and increase of thrombin activity, according to the embodiments herein. With respect to FIG. 1, an increase in thrombin content in the site of infection causes a break up in peptide chains and release of inactive gentamycine. Inactive gentamycine changes to active gentamycine in the presence of Leucin Aminopeptidase enzyme (LAP) in infectious wounds and acts upon.

Figure 2A:
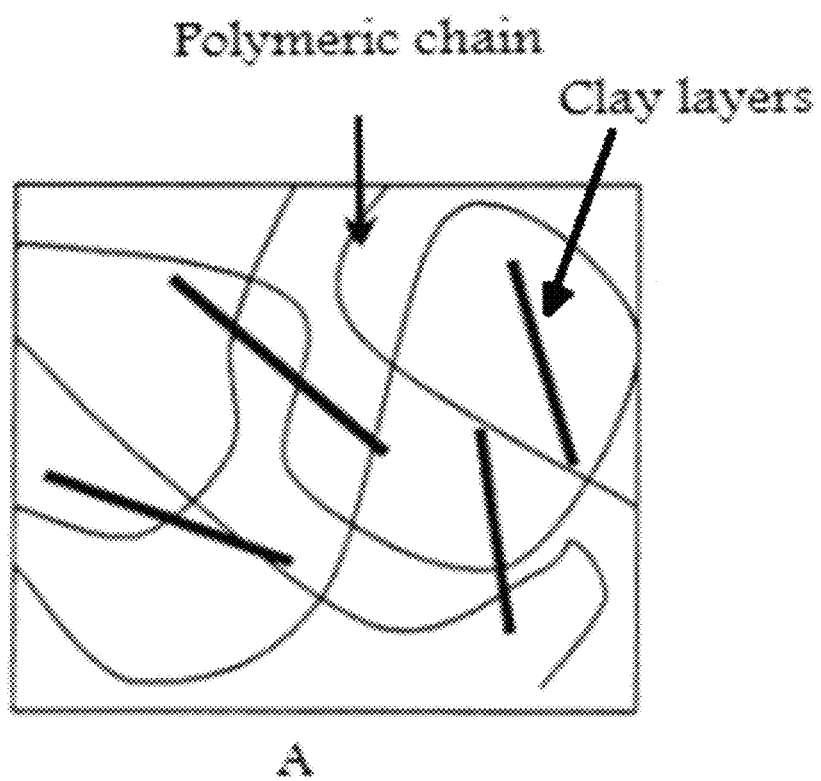
FIG. 2A shows a plan of distance between nanocomposite clay layers in polymeric hydrogel before swelling and FIG. 2B shows a plan of distance between nanocomposite clay layers in polymeric hydrogel after swelling.
Figure 2B:
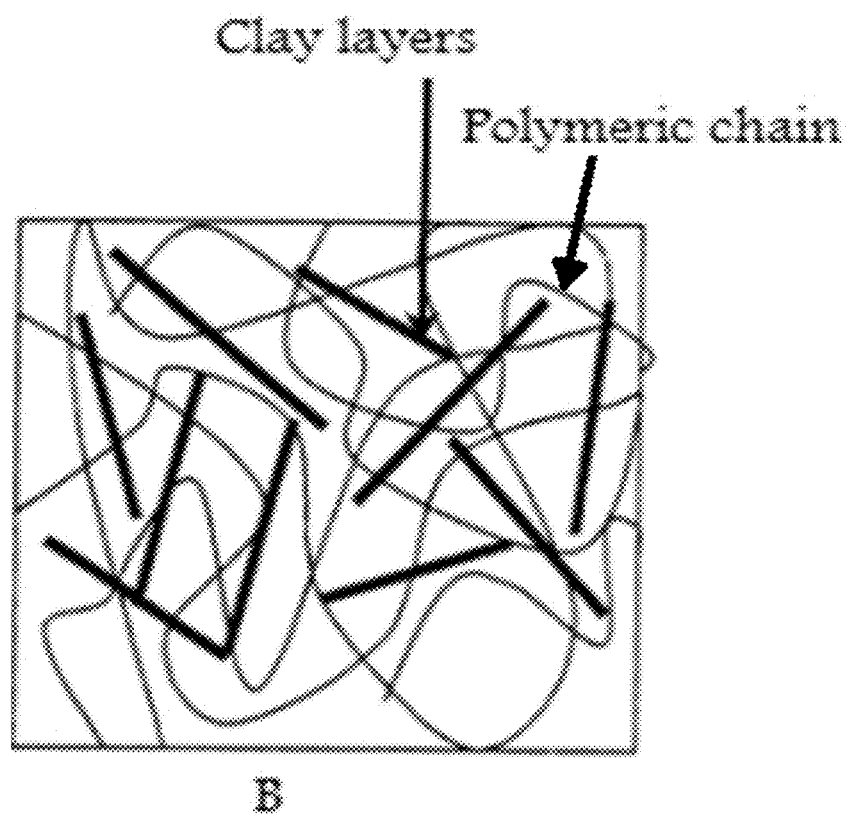

FIG. 2A shows a plan of distance between nanocomposite clay layers in polymeric hydrogel before swelling and FIG. 2B shows a plan of distance between nanocomposite clay layers in polymeric hydrogel after swelling. With respect to FIG. 2A and FIG. 2B, an increase in distance of nanocomposite clay layers after swelling can be seen. With respect to FIG. 2B, the structure after swelling is more heterogeneous. Presence of clay particles as reinforcement in nanocomposite structure causes major changes in swelling behavior in comparison with pure gels. Distribution of non-continuous silicate clay layers in continuous polymeric phase is one of the most effective factors on polymer-clay nanocomposite properties. Homogenous distribution of clay layers improves the properties and functions of the composite. Separately placing of silicate clay layers in polymeric phase may cause by an inaccurate composition without any penetration of polymeric chains between layers and leads to produce a two-phase microcomposite without desired properties. In an accurate composition, polymeric chains penetrate into clay layers and improve the nanocomposite properties.

Figure 3:
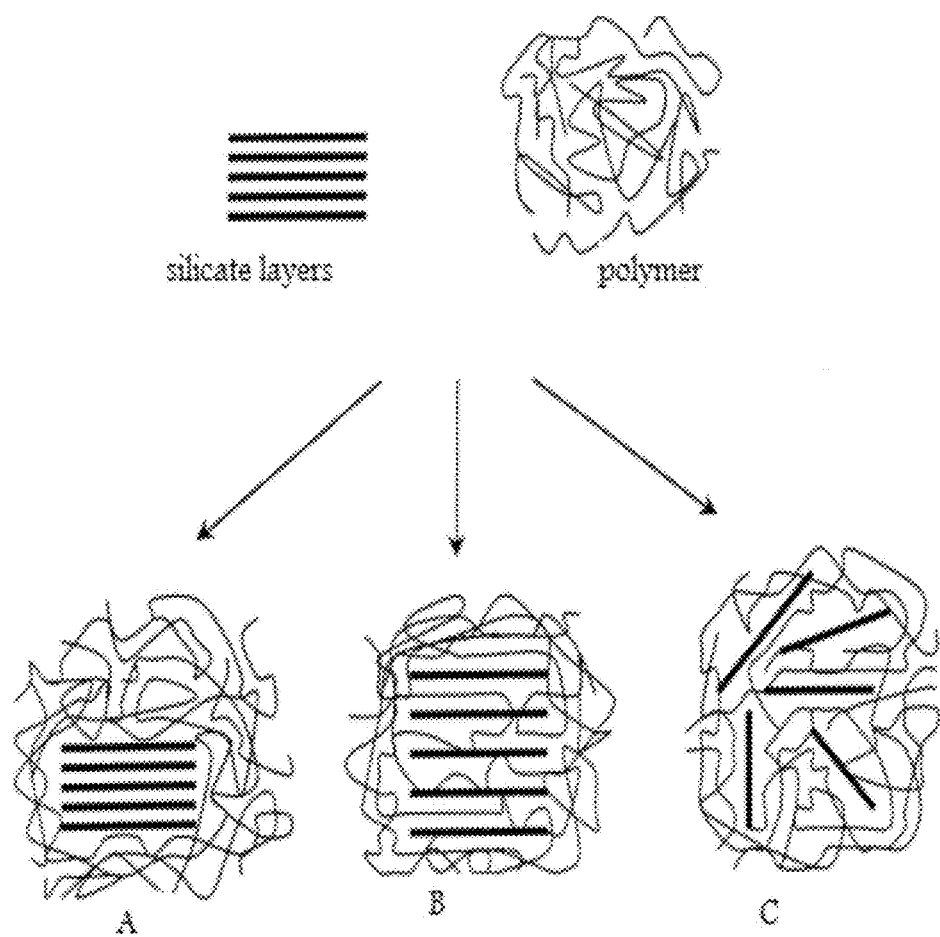
FIG. 3 shows different possible arrangements of silicate or clay layers in a hydrogel nano composite wound dressing material according to an embodiment herein.

FIG. 3 shows different possible arrangements of silicate or clay layers. With respect to FIG. 3, A shows arrangement of silicate layers in two phase microcomposite, B and C shows different arrangement of silicate layers in penetration nanocomposite. The event can maintain primary order of clay layers or change it.

Figure 4:
FIG. 4 shows transparency of a wound dressing material, according to an embodiment herein.

FIG. 4 shows transparency of wound dressing material, according to an embodiment herein. With respect to FIG. 4, transparency of wound dressing has been shown as an important factor to control the wound side infection.

Structure and distribution of clay layers in polymer-clay nanocomposite depend on properties of matrix and reinforcement phases, preparation and composition methods. Determination of this nanocomposite structure is experimentally possible. XRD and TEM are two widely used methods in structure characterization. Several tests were done to investigate the material characterization and its properties. XRD, SEM, mechanical tests according to ASTM-1882-L, hardness according to ASTM D-2240 and WVTR according to pharmacopoeia standard were done.

In this work, PVA hydrogel nanocomposite and modified and non modified montmorillonite are used for new wound dressing. Montmorillonite, saponite and hectorite are the most common silicate layers with many applications.

Hydrophilic properties of silicate layers are necessary for using them in organic environment. Van der waal forces are the major force between layers which helps the penetration of small molecules among silicate layers. This ability is applied for surface modification of silicate layers. One of these methods is replacing hydrate cations with other cations like ammonium alkyl and phosphonium alkyl. The method in the embodiments herein, changes the clay nature into hydrophobic which is more compatible in organic environment and decreases surface energy. Clays are not compatible with organic materials like polymeric matrixes used in polymeric nanocomposites because of hydrophilic properties of clays. In addition distribution of this phase depends on its nature. Surface modification of clay particles provides a more homogenous distribution. Surface modification is done by replacing inorganic clay cations with organic cations to satisfy required compatibility with organic phases. Bases metals like Na, K and Li are widely used in this replacement. These cations are provided by long carbon chains with more than 12 carbon atoms and its concentration determines the speed of reaction.

Figure 5:
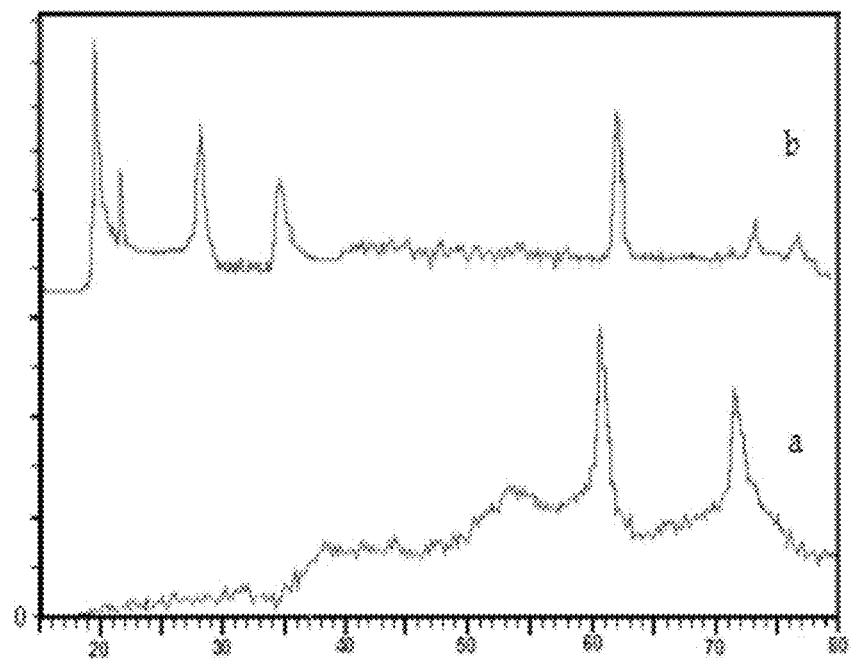
FIG. 5 shows XRD patterns for non-modified montmorillonite (MONT) and modified montmorillonite (OMONT) in a wound dressing material, according to an embodiment herein, where (a) shows XRD pattern for MONT and (b) shows XRD pattern for OMONT.

FIG. 5 shows XRD patterns for non-modified montmorillonite (MONT) and modified montmorillonite (OMONT) where (a) shows XRD pattern for MONT and (b) shows XRD pattern for OMONT. With respect to FIG. 5, the maximum of absorbance peak is higher for MONT in comparison with OMONT. So, there is more interlayer space in OMONT.

Figure 6:
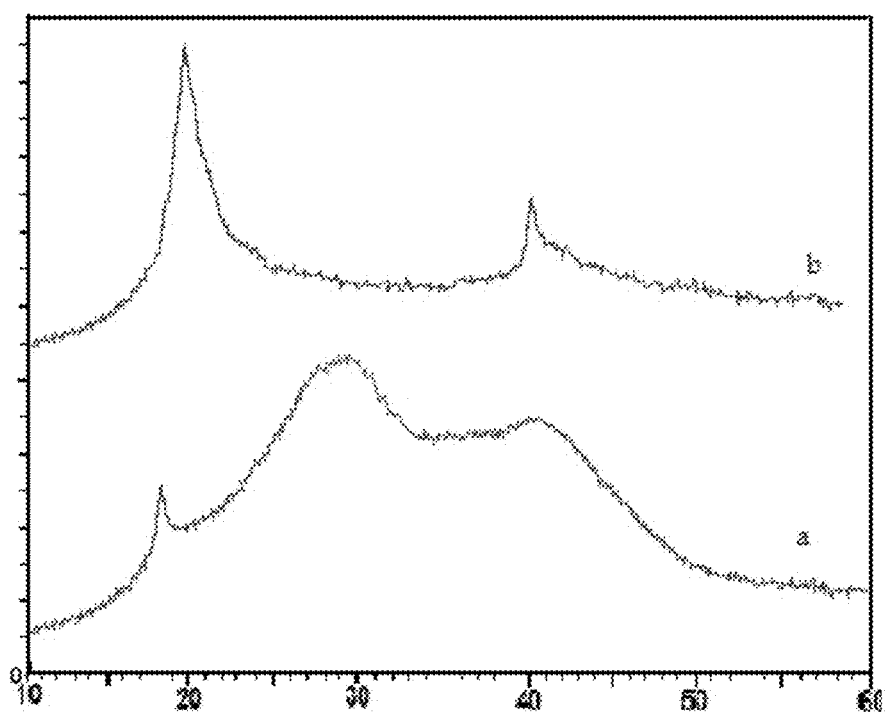
FIG. 6 shows XRD patterns for hydrogel nanocomposite containing 5% non-modified montmorillonite (MONT) and 5% modified montmorillonite (OMONT) in a wound dressing material, according to an embodiment herein, where (a) shows XRD pattern for hydrogel containing 5% MONT and (b) shows XRD pattern for hydrogel containing 5% OMONT.

FIG. 6 shows XRD patterns for hydrogel nanocomposite containing 5% non-modified montmorillonite (MONT) and 5% modified montmorillonite (OMONT), where (a) shows XRD pattern for hydrogel containing 5% MONT and (b) shows XRD pattern for hydrogel containing 5% OMONT. With respect to FIG. 6, the maximum of absorbance peak is higher for MONT in comparison with OMONT. Consequently, distribution of OMONT clay in nanocomposites is better than MONT. The results confirmed the role of MONT in producing penetrate structure and changing in silicate layer orders. However, there is no change in silicate layer orders in presence of OMONT.

Figure 7A:
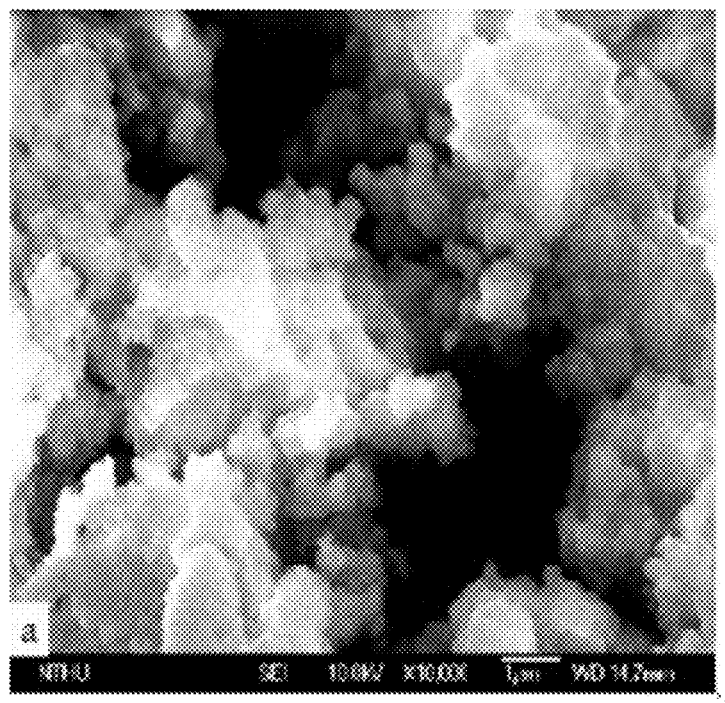
FIG. 7A shows SEM image of a pure PVA in a wound dressing material, according to an embodiment herein.
Figure 7B:
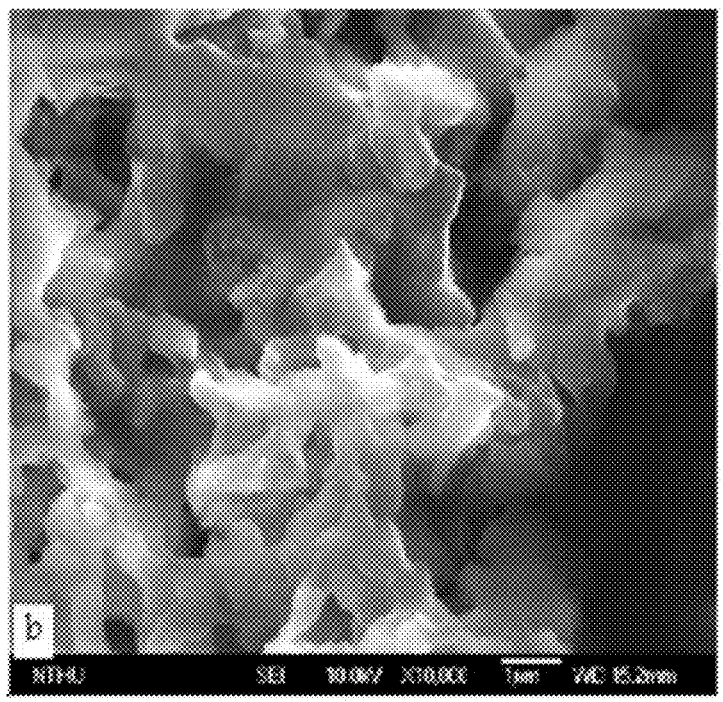
FIG. 7B shows SEM image of nanocomposite hydrogel containing 5% clay i.e. 5% modified montmorillonite (OMONT) in a wound dressing material, according to an embodiment herein.
Figure 7C:
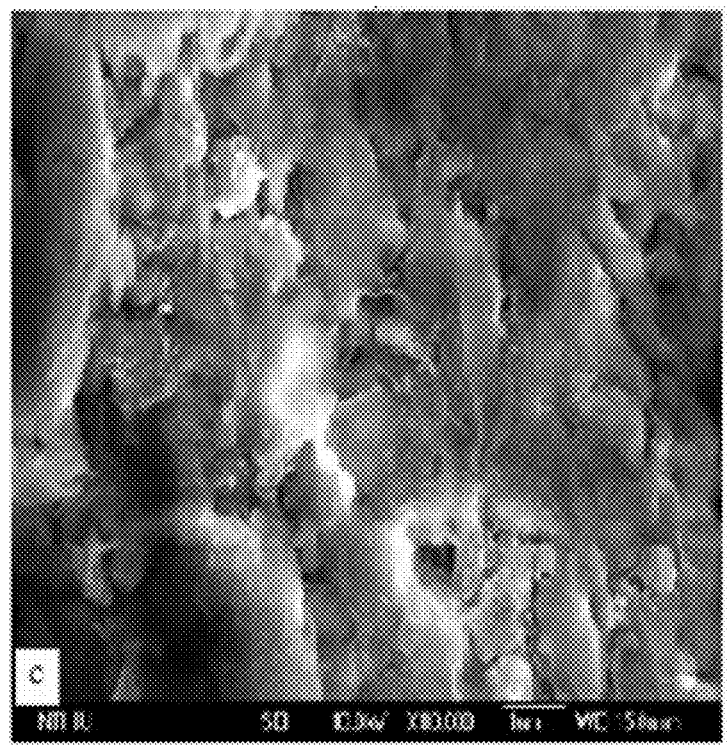
FIG. 7C shows SEM image of nanocomposite hydrogel containing 5% clay i.e. 5% non-modified montmorillonite (MONT), according to an embodiment herein.

FIG. 7A shows SEM image of a pure PVA. FIG. 7B shows SEM image of nanocomposite hydrogel containing 5% clay i.e. 5% modified montmorillonite (OMONT). FIG. 7C shows SEM image of nanocomposite hydrogel containing 5% clay i.e. 5% non-modified montmorillonite (MONT). With respect to FIG. 7A, FIG. 7B and FIG. 7C, the pure PVA showed a more porous structure with less cross linking in comparison with nanocomposite hydrogel. It means presence of clay (MONT and OMONT) act as cross-linking mediator. In addition, the role of MONT is more significant than OMONT in cross-linking. The microstructure of OMONT nanocomposite is more porous with higher degree of crystal order.

Figure 8:
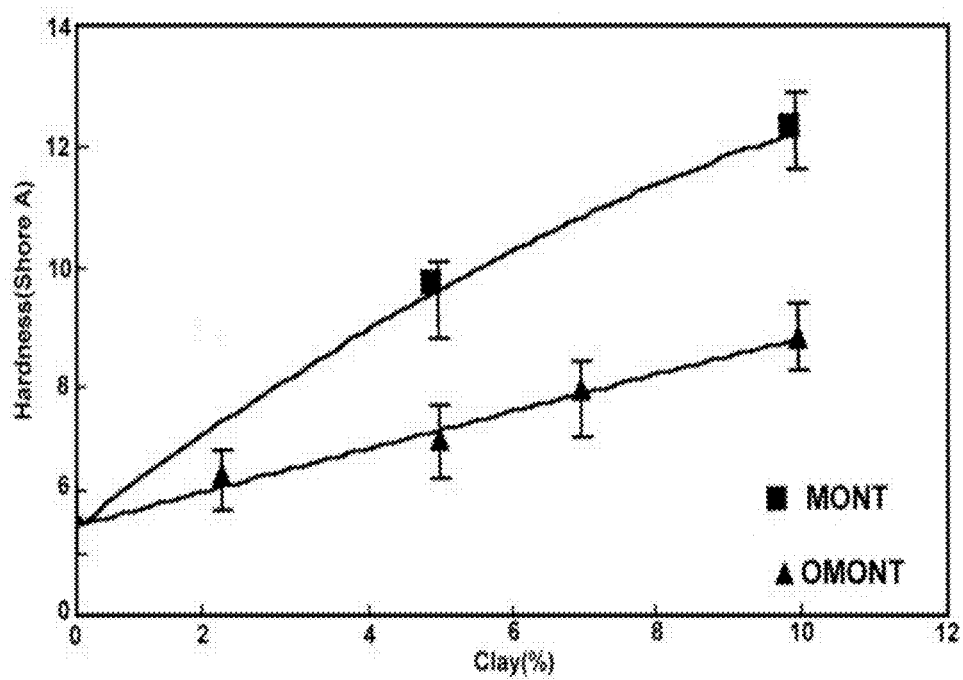
FIG. 8 shows a hardness measurement of modified and non-modified montmorillonite with different clay percentages in a wound dressing material, according to an embodiment herein.

FIG. 8 shows hardness measurement of modified and non-modified montmorillonite in different clay percentage. With respect to FIG. 8, increasing the amount of clay content increases the hardness of nanocomposite hydrogel. On the other hand, hydrogels containing MONT are harder than those containing OMONT in a same content of clay. Desired hardness of these hydrogels in the range of 5.7-12 omits the unfavorable adherence between wound surface and wound dressing.

Figure 9:
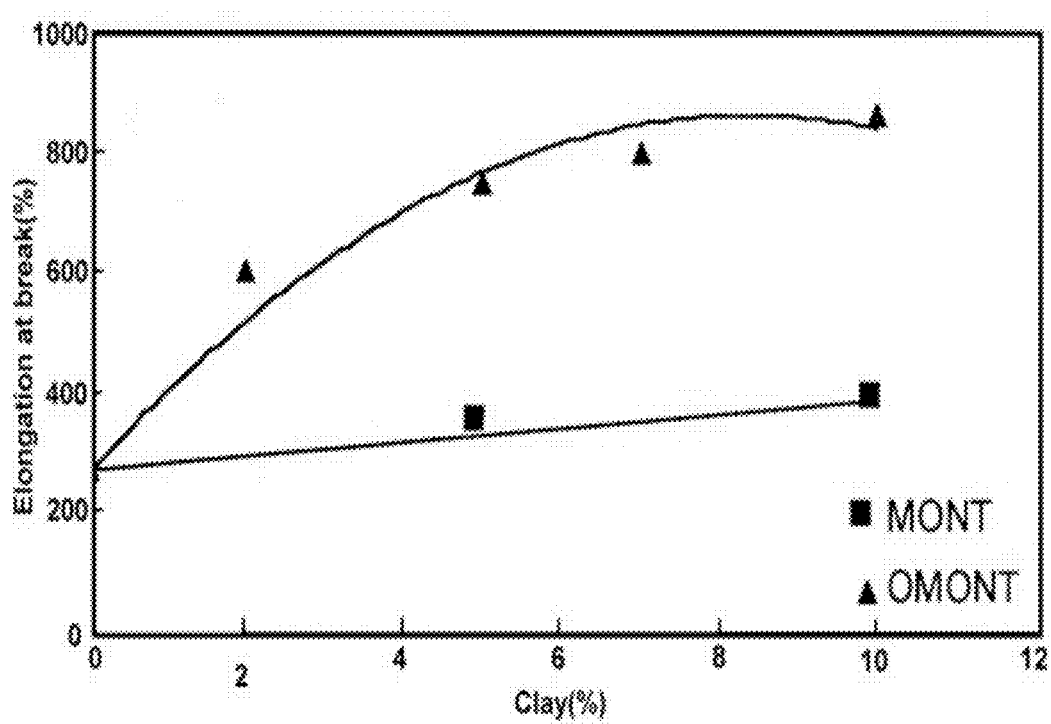
FIG. 9 shows a percentage elongation of modified and non modified montmorillonite in different clay percentages in a wound dressing material, according to an embodiment herein.

FIG. 9 shows percentage elongation of modified and non modified montmorillonite in different clay percentages. Mechanical examinations proved presence of montmorillonite improve the elastic properties caused a significant increase in elongation up to 2 fold. With respect to FIG. 9, OMONT is more effective in this increase of elongation and Young modulus.

Figure 10:
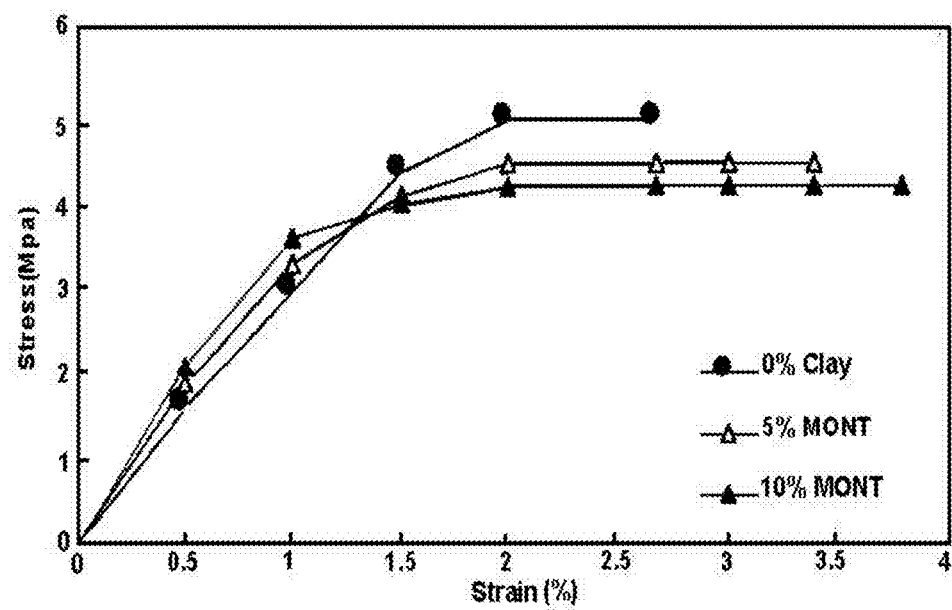
FIG. 10 shows a stress-strain curve for nanocomposite hydrogel containing non-modified montmorillonite (MONT) in a wound dressing material, according to an embodiment herein.
Figure 11:
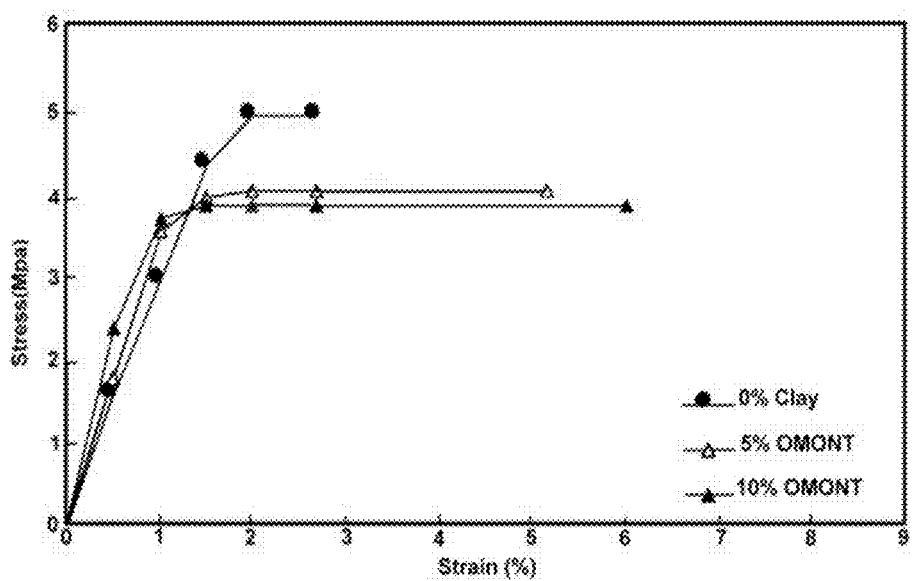
FIG. 11 shows a stress-strain curve for nanocomposite hydrogel containing modified montmorillonite (OMONT) wound dressing material, according to an embodiment herein.

FIG. 10 shows a stress-strain curve for nanocomposite hydrogel containing non-modified montmorillonite (MONT) and FIG. 11 shows a stress-strain curve for nanocomposite hydrogel containing modified montmorillonite (OMONT). With respect to FIG. 10 and FIG. 11 a similar behavior of both nanocomposite hydrogels containing MONT and OMONT is observed.

Figure 12:
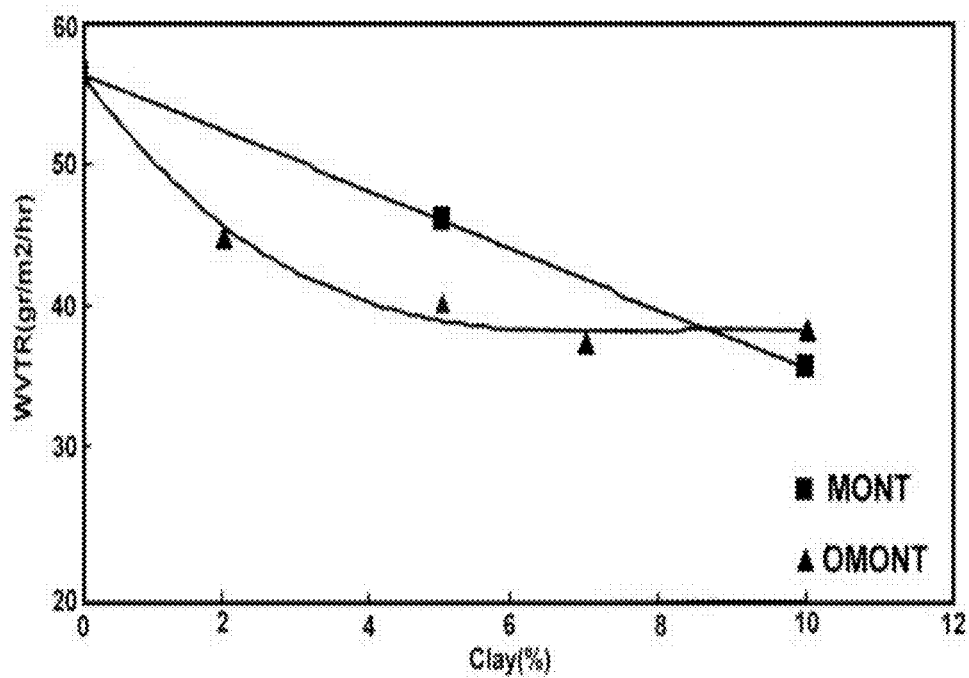
FIG. 12 shows Water Vapor Transforming Rate (WVTR) of modified and non-modified MONT in different clay percentages in a wound dressing material, according to an embodiment herein.

FIG. 12 shows Water Vapor Transforming Rate (WVTR) of modified and non-modified montmorillonite in different clay percentages. High water vapor transforming rate (WVTR) one of the most important parameters should be considered in hydrogel wound dressing properties which can determine the wound dressing ability to transform water vapor. WVTR improves the wound treatment and prevent from infection caused by concentration of wound liquids. With respect to FIG. 12, clay can change WVTR and increasing MONT or OMONT content decrease the evaporation rate. In general, silicate clay layers behave as physical dams and decrease WVTR of hydrogel nanocomposite by preventing of vapor transformation.

Figure 13A:
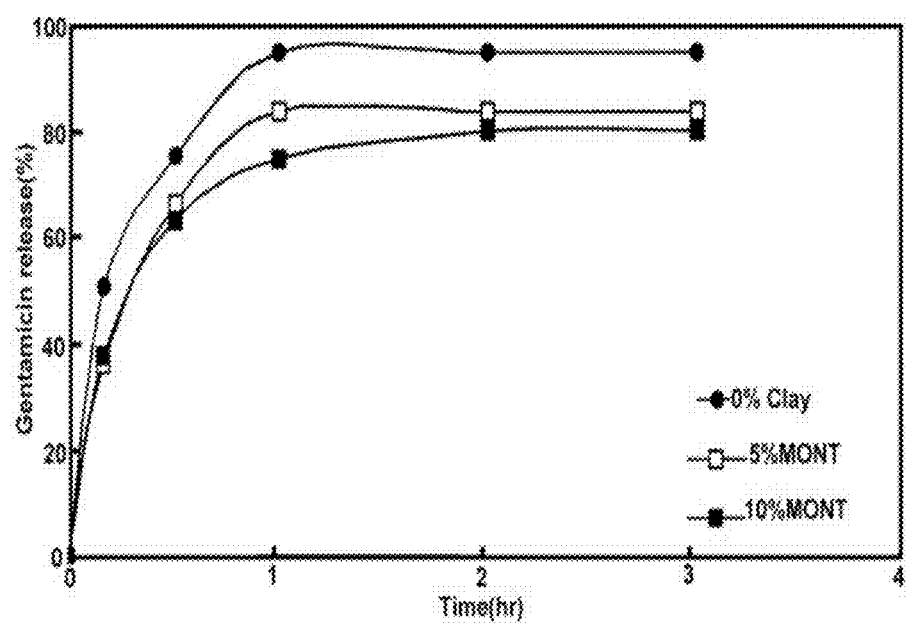
FIG. 13A illustrates a drug release profile showing the drug release percentages in different samples during a short period of dressing with a wound dressing material, according to an embodiment herein
Figure 13B:
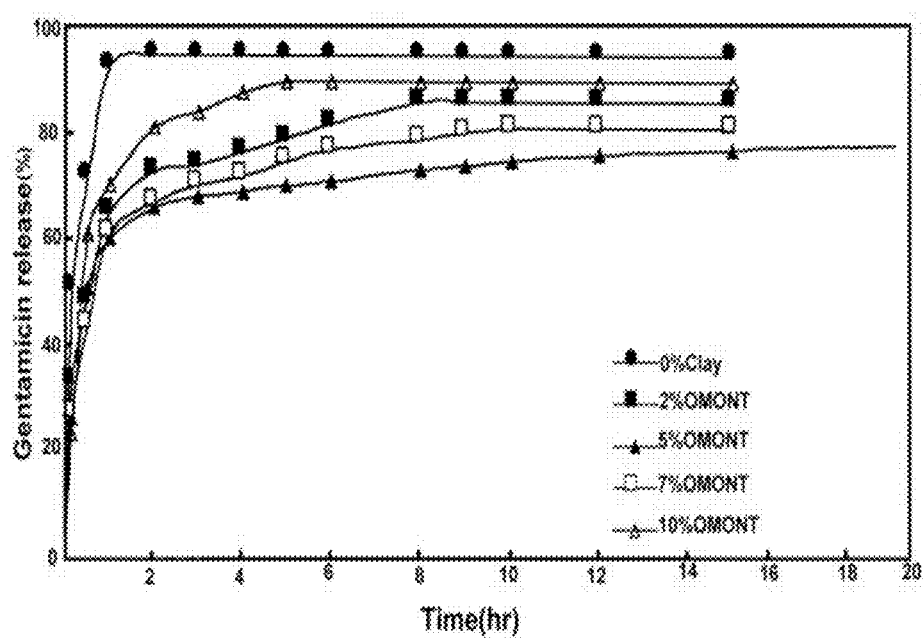
FIG. 13B shows a drug release profile showing the drug release percentages in different samples for a long period of dressing with a wound dressing material, according to an embodiment herein.

FIG. 13A illustrates a drug release profile showing the drug release percentages in different samples for a short period of dressing and FIG. 13B shows a drug release profile showing the drug release percentages in different samples for a long period of dressing. With respect to FIG. 13A and FIG. 13B, it has been investigated that drug release is lower in OMONT contained samples than pure hydrogel. The lower amount of drug release confirms presence of extra dams in their structure produced by clay. These dams caused a delay in drug release for about 5 to 20 hours depend on OMONT content. The lower speed of drug release is a major property in wound dressing application achieved by an optimum content of clay.

Drug release tests were performed for pure PVA and PVA containing MONT. Drug release tests showed the highest release rate in pure PVA i.e. without clay. Hydrogel nanocomposite containing MONT illustrated a same behavior in gentamycine release.

Example 1

Following the described procedure a nanocomposite hydrogel was prepared. Briefly, the following three steps were done:
Carboxylation of nanocomposite hydrogel
Linking of peptide chain into nanocomposite chain
Linking of gentamycine into peptide chain Carboxylation of nanocomposite hydrogel: 10 g of prepared hydrogel (samples No. 8 to 14) was added to 300 g Dimethylsolfoxide containing 1.6 g of succinic anhydride and 0.6 g of pyridine. Solution was held at 10° C. for an overnight to complete the reaction. After that, the resultant hydrogel (PVA-COOH) was extracted from the solution and was washed with PBS several times to remove unreacted materials.

Linking of peptide chain into nanocomposite chain: All the samples were washed with dimethyl formamide several times to obtain composed of peptide-nanocomposite hydrogel and then were placed in a solution of 10 cc formamide containing 50 mg N-Hydroxysuccinimide (HOSU) and 80 mg 1-Ethyl-3-(3-dimethylaminopropyl)carbodiimide hydrochloride (EDC) and held for an overnight. The samples were brought out of solution and were washed with dimethyl formamide and DDW several times. All of the samples were placed in a solution of 120 mg peptide for 24 h to create links between peptide chains and carboxyl groups. Some of the samples were tested to analyze amount of peptide chains linked to network and others were used to prepare wound dressing containing gentamycine.

Linking of gentamycine into peptide chain: 5 g of each samples prepared in the previous step were washed with PBS several times to remove all remaining unreacted materials. Mechanical stirring of samples in a solution of 7 g of gentamycine and 25 mg of EDC was applied for 24 h for linking of gentamycine and peptide chain. Then, all the samples were washed with PBS and deionized water further more and placed in +4° C.

Equilibrium water contained in the nanocomposite is another important property. It is defined as the period taken to stop the absorbance of water and reach to equilibrium condition for samples swelling in water. This term determine the time that wound dressing should be replaced. This period increases by increasing clay content. Increasing of OMONT content shows a same behavior like clay. It means that using OMONT provide an excellent function in wound dressing with a few required replacement. Presence of MONT and OMONT (modified montmorillonite) nano clay particles improve mechanical properties of wound dressing. The optimum percentage of MONT controls drug release with the best rate.

The embodiments herein provide a method to produce and manufacture a desired drug release system for the purposes of controlled release. The system provides a wound dressing with an ability to release antibiotics during microbial infection to prevent the patient from diseases caused in liver and kidney after a long time use of antibiotics and makes the bacteria resistant to drugs.

The embodiments herein provide a nanocomposite wound dressing made up of hydrogel-clay with antibiotic. The antibiotic is linked into three dimensional (3D) structure of nanocomposite via an infection sensitive peptide link. The antibiotic in the embodiments herein is gentamycine.

The wound dressing is composed of absorbent materials with high transparency. Fracture of peptide chains leads to release of drug in the site of infectious wound. Presence of nano clay particles increases the releasing time which makes the wound dressing more desired and improves its mechanical properties and swelling behavior.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A hydrogel nanocomposite wound dressing comprising:
   a polymeric basal matrix, wherein the polymeric basal matrix is made up of polyvinyl alcohol polymer with an amount of 1-15% by weight;
   a reinforcing agent, wherein the reinforcing agent comprises clay nanoparticles to inhibit a sudden drug release, wherein the clay nanoparticles comprises montmorillonite nano particles with an amount of 0-2% by weight;
   a biological sensor, wherein the biological sensor is a peptide chain, wherein the peptide chain is thrombin sensitive with a presence amount of 50 to 200 mg, and the peptide chain is Gly-(D)Phe-Pro-Arg-Gly-Phe-Ala-Gly-Gly; and
   an antibiotic with an amount of 1-3% by weight, and wherein the antibiotic is slowly released in a wound.

2. The wound dressing according to claim 1, wherein the polyvinyl alcohol polymer has a degree of polymerization of 1700.

3. The wound dressing according to claim 1, wherein the polyvinyl alcohol polymer has a molecular weight of 26300-30000.

4. The wound dressing according to claim 1, wherein the montmorillonite nano particles have a saponification value of greater than 98%.

5. The wound dressing according to claim 1, wherein the montmorillonite nanoparticles are both modified and non-modified montmorillonite nanoparticles.

6. The wound dressing according to claim 1, wherein the modified and non modified montmorillonite nanoparticles have a particle size of about 2 nm.

7. The wound dressing according to claim 1, wherein the antibiotic is gentamycine.

8. The wound dressing according to claim 1, wherein the hydrogel nanocomposite wound dressing is transparent.

9. The wound dressing according to claim 1, wherein the antibiotic is released in 20 hours and reaches to a maximum level in first 2 hours, and wherein the antibiotic is released after a breaking down of the peptide chain.

10. The wound dressing according to claim 1, wherein the hydrogel nanocomposite wound dressing is infection absorbent and prevents from infection in non-infectious wounds by preventing a microbial permeation and wherein the hydrogel nanocomposite wound dressing is non-toxic.

11. The wound dressing according to claim 1, wherein the hydrogel nanocomposite wound dressing treats infectious wound without a need for a repetitive replacement.

12. A method of synthesizing a hydrogel nanocomposite wound dressing comprises:
   carboxylating a Polyvinyl alcohol nanocomposite hydrogel structure;
   linking a peptide chain with the carboxylated PVA nanocomposite hydrogel structure; and
   linking an antibiotic with a peptide chain, wherein the antibiotic is gentamycin and wherein the peptide chain is Gly-(D)Phe-Pro-Arg-Gly-Phe-Ala-Gly-Gly.

13. The method according to claim 12, wherein the step of carboxylating a PVA nanocomposite hydrogel structure includes:
   preparing aqueous solutions of Polyvinyl alcohol (PVA) with a percentage of 1-15% and a clay with a percentage of 1-10%;
   providing a thermal treatment process to the prepared aqueous solutions of the PVA and the clay, wherein the thermal treatment process involves a heating and a cooling of the solutions, wherein the heating involves heating the prepared aqueous solutions of the PVA and the clay at +20° C. for 24 hours and wherein the cooling involves cooling the prepared aqueous solutions of the PVA and the clay at −20° C. for 24 hours, wherein the process is performed twice;
   carboxylating the thermally treated solution by adding dimethyl sulfoxide;
   adding succinic anhydride and pyridine to the thermally treated solution added with dimethyl sulfoxide;
   holding the thermally treated solution added with dimethyl sulfoxide, succinic anhydride and pyridine at 10° C. for an overnight to complete the carboxylation reaction;
   extracting a resultant hydrogel;
   washing the extracted resultant hydrogel with Phosphate Buffer Saline (PBS) to obtain a first resultant solution;
   washing the first resultant solution with Distilled Deionized Water (DDW) for several times to obtain a second resultant solution;
   washing the second resultant solution with dimethyl formamide for several times to remove unreacted materials.

14. The method according to claim 12, wherein the step of linking a peptide chain with the carboxylated PVA nanocomposite hydrogel structure includes:
   holding the washed carboxylated PVA nanocomposite hydrogel with a solution of formamide having a volume of 10 cc to obtain a sample, wherein the solution of formamide contains 50 mg of N-Hydroxysuccinimide (HOSU) and 80 mg of 1-Ethyl-3-(3-dimethylaminopropyl)carbodiimide (EDC);

placing the sample in a solution of peptide chain with an amount of 120 mg for an overnight; and washing the sample placed in a solution of peptide chain with PBS for several times to remove all remaining unreacted materials.

15. The method according to claim 12, wherein the step of linking the gentamycine with the peptide chain includes mechanically stirring a solution of linked peptide with carboxylated PVA nanocomposite hydrogel for 24 hours in a solution comprising gentamycin with an amount of 7 g and EDC with an amount of 25 mg.

* * * * *